United States Patent
Daniels et al.

(10) Patent No.: US 10,668,254 B2
(45) Date of Patent: Jun. 2, 2020

(54) STABILIZING AND SEALING CATHETER FOR USE WITH A GUIDING CATHETER

(71) Applicant: Radius Medical, LLC, Hudson, MA (US)

(72) Inventors: David Daniels, San Carlos, CA (US); Richard M. DeMello, Stow, MA (US); Maureen Finlayson, Stow, MA (US); Jonathan R. DeMello, Stow, MA (US)

(73) Assignee: Radius Medical LLC, Hudson, MA (US)

(*) Notice: Subject to any disclaimer, the term of this patent is extended or adjusted under 35 U.S.C. 154(b) by 0 days.

(21) Appl. No.: 14/834,910

(22) Filed: Aug. 25, 2015

(65) Prior Publication Data

US 2016/0051799 A1    Feb. 25, 2016

Related U.S. Application Data

(60) Provisional application No. 62/041,401, filed on Aug. 25, 2014, provisional application No. 62/189,350, filed on Jul. 7, 2015.

(51) Int. Cl.
*A61M 25/10* (2013.01)
*A61M 25/00* (2006.01)

(52) U.S. Cl.
CPC ........ *A61M 25/10* (2013.01); *A61M 25/1011* (2013.01); *A61M 2025/0018* (2013.01);
(Continued)

(58) Field of Classification Search
CPC .. A61M 2025/0018; A61M 2025/0681; A61M 2025/004; A61M 2025/09008;
(Continued)

(56) References Cited

U.S. PATENT DOCUMENTS

| | | | |
|---|---|---|---|
| 4,832,028 A | 5/1989 | Patel | |
| 5,158,540 A * | 10/1992 | Wijay | A61M 25/0054 604/101.05 |

(Continued)

FOREIGN PATENT DOCUMENTS

WO    WO 2014036530 A1 *    3/2014    ........ A61M 25/003

OTHER PUBLICATIONS

Jean-François Surmely, et al., Variation on the Anchor balloon technique for difficult stent delivery, Case Report, Kardiovaskuläre Medizin 2007;10: Nr 12, pp. 397-399.
(Continued)

*Primary Examiner* — Kevin C Sirmons
*Assistant Examiner* — Alexandra Lalonde
(74) *Attorney, Agent, or Firm* — Cesari and McKenna, LLP

(57) ABSTRACT

A coaxial stabilizing and sealing catheter provides increased support to a guide catheter that is seated in an ostium of a branch artery by extending through and out of a distal end of the guide catheter and anchoring in position within the vessel that is being treated. The stabilizing and sealing catheter includes, as part of a relatively flexible distal section, a balloon that locks the distal end of the stabilizing and sealing catheter in place to provide support to the therapeutic devices that are introduced and further seals the artery to prevent blood from entering the artery. A sealing cuff at a proximal end of the stabilizing and sealing catheter provides a seal between the exterior of the stabilizing and sealing catheter and the interior of the guide catheter. In addition, a fixing mechanism it utilized to lock the guide catheter in place to exchange therapeutic devices.

17 Claims, 9 Drawing Sheets

(52) U.S. Cl.
CPC .............. *A61M 2025/1052* (2013.01); *A61M 2025/1056* (2013.01); *A61M 2025/1079* (2013.01)

(58) Field of Classification Search
CPC .......... A61M 2025/09166; A61M 2025/0183; A61M 2025/0006; A61M 2025/1015; A61M 2025/1063; A61M 2025/1013; A61M 2025/1056; A61M 2025/1079; A61M 2025/1061; A61M 2025/1054; A61M 25/0026; A61M 25/1006; A61M 25/0071; A61M 25/1011; A61M 25/10; A61M 2025/09125; A61M 2025/0186; A61M 25/09041; A61M 2025/1059; A61M 2025/0079; A61M 2025/0175

See application file for complete search history.

(56) References Cited

U.S. PATENT DOCUMENTS

| | | | | |
|---|---|---|---|---|
| 5,730,734 | A * | 3/1998 | Adams ................. | A61M 25/00 604/167.02 |
| 6,299,628 | B1 * | 10/2001 | Harrison ........... | A61M 25/0105 606/194 |
| 6,960,222 | B2 * | 11/2005 | Vo ......................... | A61B 17/12 604/103.07 |
| 8,048,032 | B2 | 11/2011 | Root et al. | |
| 2002/0165574 | A1 * | 11/2002 | Ressemann ...... | A61B 17/12045 606/194 |
| 2002/0165598 | A1 * | 11/2002 | Wahr ............... | A61B 17/12045 623/1.11 |
| 2007/0225677 | A1 * | 9/2007 | Rowe ................. | A61M 25/1011 604/509 |
| 2007/0293719 | A1 * | 12/2007 | Scopton ............. | A61B 1/00098 600/106 |
| 2012/0238954 | A1 * | 9/2012 | You ....................... | A61M 29/02 604/103.1 |
| 2012/0296364 | A1 * | 11/2012 | Gundale ............. | A61M 25/005 606/192 |
| 2012/0302996 | A1 * | 11/2012 | Barash .............. | A61M 25/1018 604/509 |
| 2015/0359547 | A1 * | 12/2015 | Vale ....................... | A61B 17/22 606/115 |
| 2016/0346515 | A1 * | 12/2016 | Buller .................. | A61M 25/01 |

OTHER PUBLICATIONS

Application and limitation of anchor technique and child mother guiding technique, Sendai Kousei Hospital, Japan, Naoto Inoue M.D. FJCC, FSCAI, TCT-ASIA 2007, 35 pages.

Fujita et al., "New technique for superior guiding catheter support during advancement of a balloon in coronary angioplasty: the anchor technique," Abstract, Catheter Cardiovasc Interv. Aug. 2003;59(4):482-8.

The Anchor-Balloon Technique for Difficult Chronic Total Occlusions, Published on *Cath Lab Digest* (http://www.cathlabdigest.com), Submitted by hmpeditor on Fri, May 3, 2013—11:34. 5 pages.

* cited by examiner

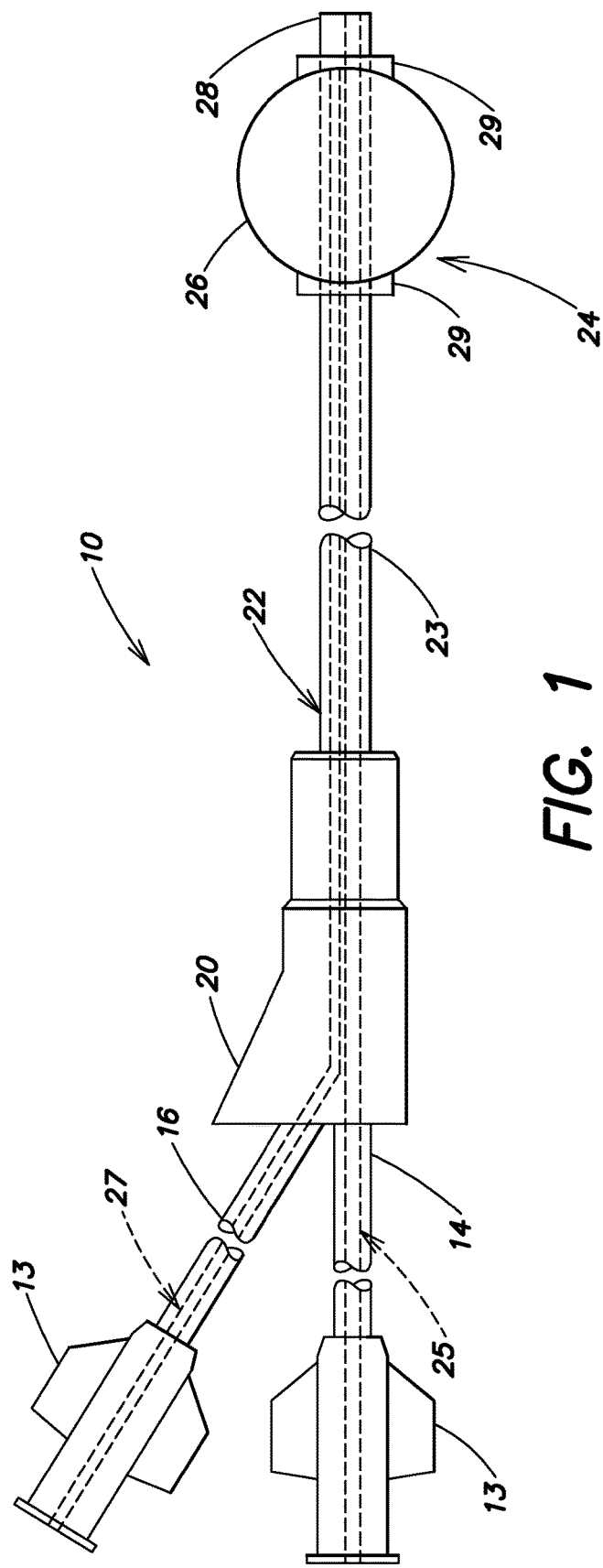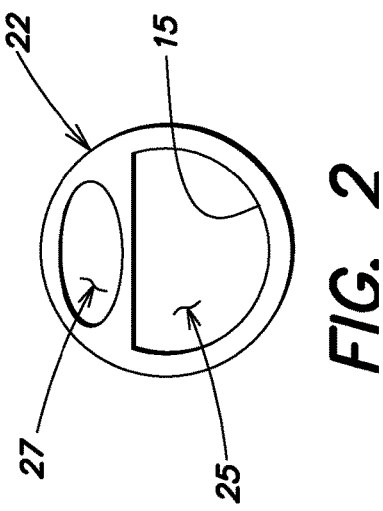
FIG. 1
FIG. 2

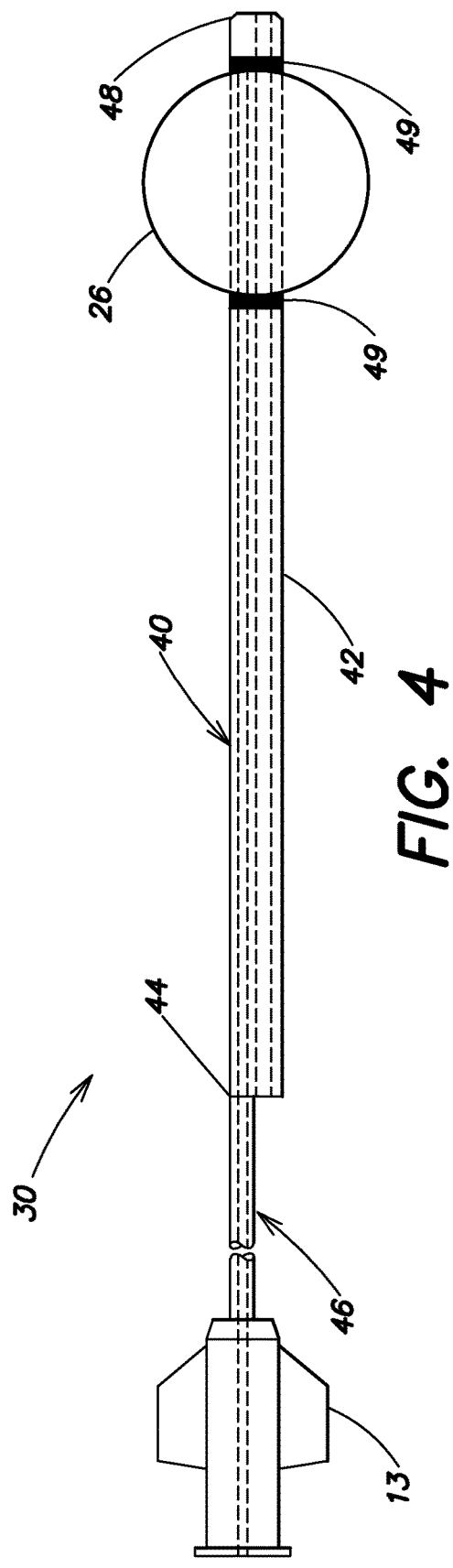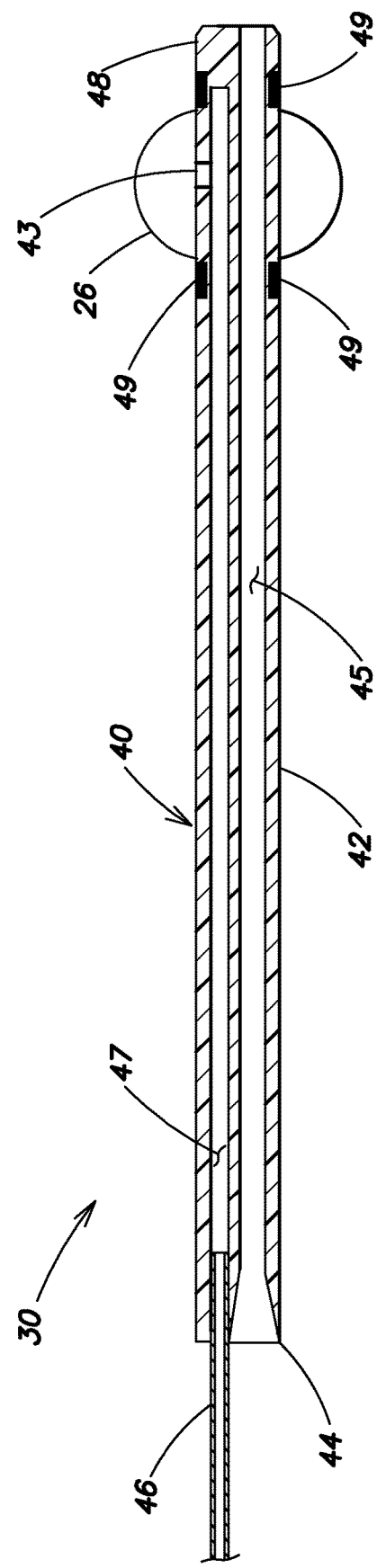

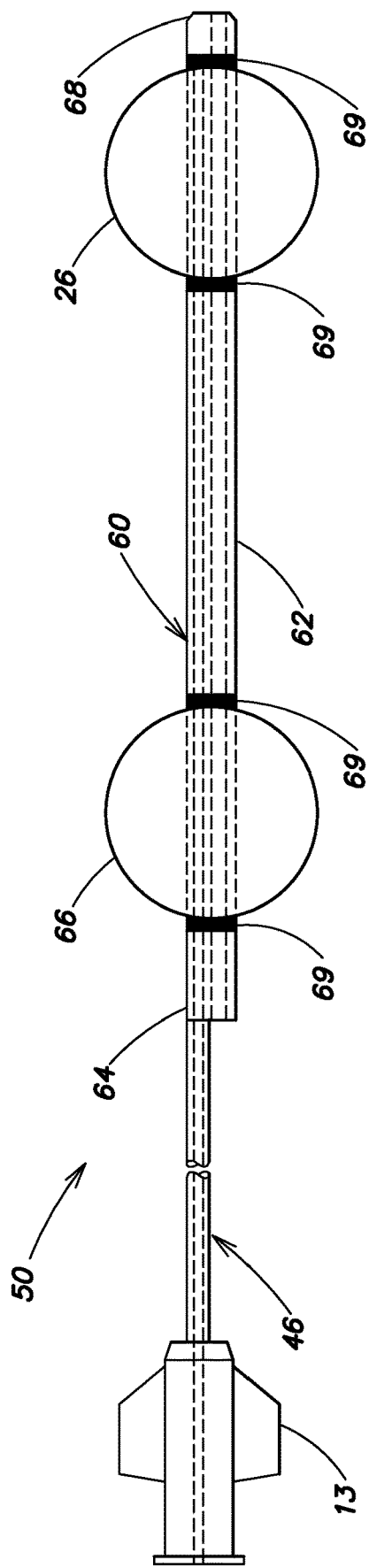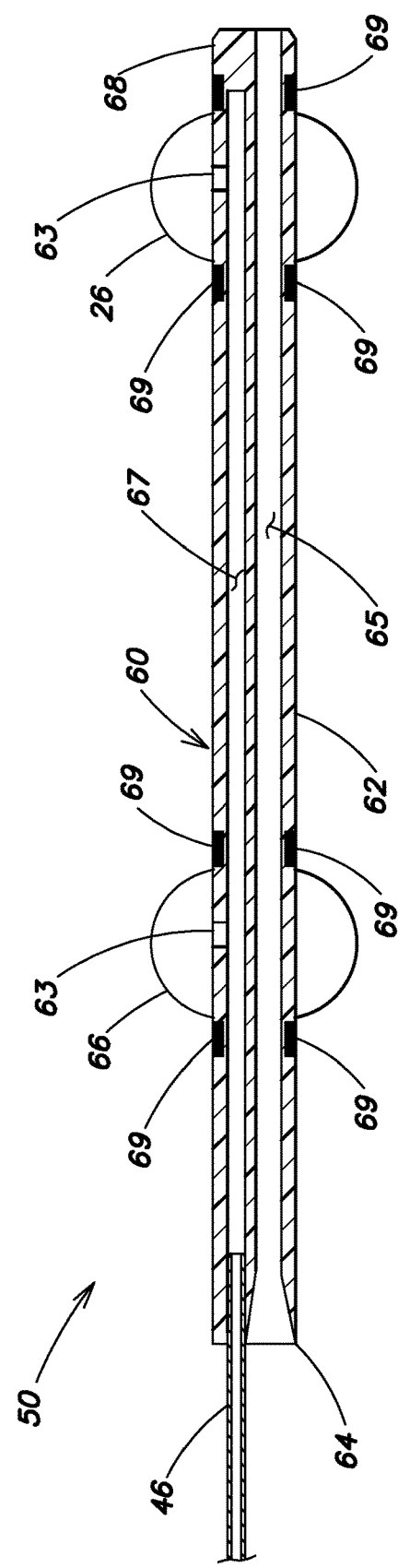

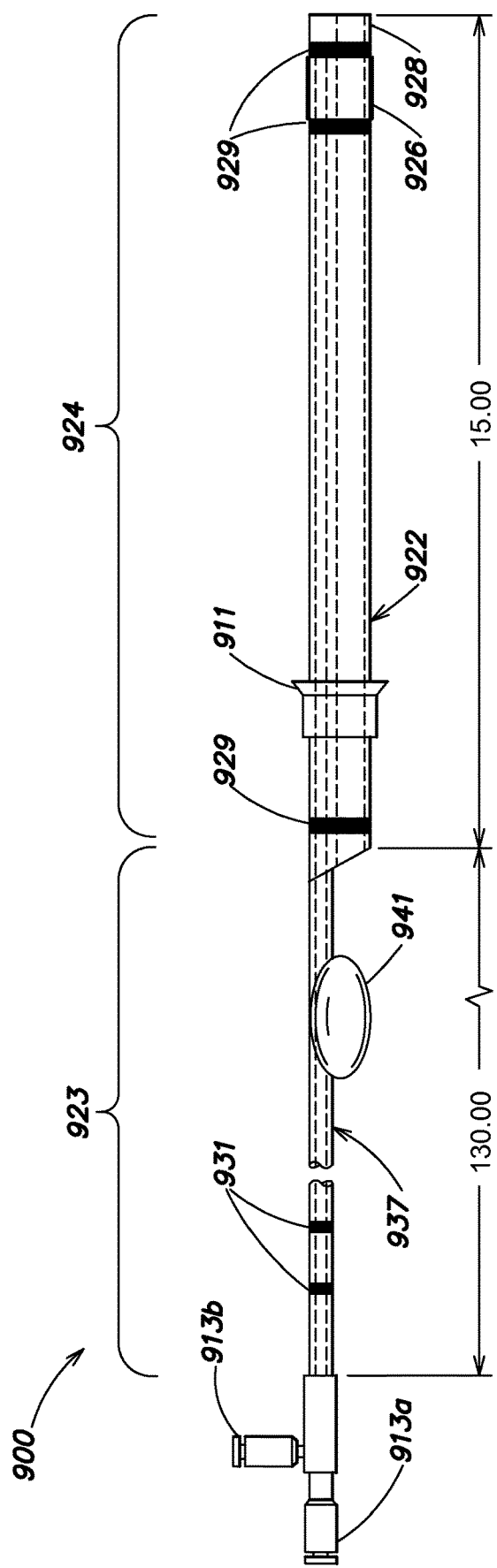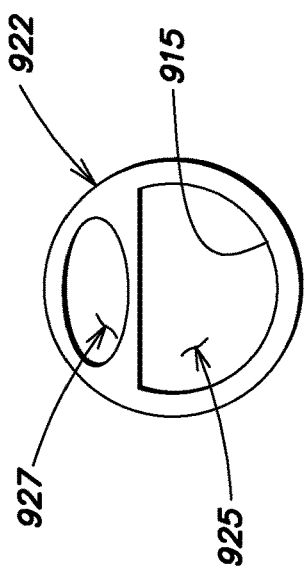
FIG. 9
FIG. 10

STABILIZING AND SEALING CATHETER FOR USE WITH A GUIDING CATHETER

RELATED APPLICATIONS

The present application claims the benefit of U.S. Provisional Application Ser. No. 62/041,401, which was filed on Aug. 25, 2014, and U.S. Provisional Application Ser. No. 62/189,350, which was filed on Jul. 7, 2015. The contents of both applications are hereby incorporated by reference in their entirety.

BACKGROUND OF THE INVENTION

Field of the Invention

The invention relates generally to guiding catheters and, more particularly, to guiding catheters for use within branch arteries.

Background Information

Guiding or guide catheters are used as conduits to introduce therapeutic devices into smaller branch arteries or vessels within the human body. Guide catheters typically consist of a large bore, single lumen plastic extrusion. They usually have a low friction inner surface, such as a polytetrafluoroethylene (PTFE) liner, to facilitate movement of the therapeutic devices within the catheter. The guide catheters are offered in various diameters and have numerous pre-shaped curve styles available on their distal segments, to accommodate the various patient anatomies that are encountered. The catheters are constructed from relatively stiff materials, such that they remain as stable as possible while the therapeutic devices are passed through and manipulated.

In use, the catheters are introduced into a main artery or vessel within the body, such as the Aorta, and directed to the opening of a branch vessel, such as a coronary artery. The leading edge (distal end) of the guide catheter is seated at the opening (ostium) of the coronary artery while the rearward end (proximal end) of the guide catheter remains exposed outside of the patient, typically through the femoral, brachial, or radial artery. The guide catheter relies on the proper pre-shaped curve style and its inherent stiffness to remain stable at the coronary ostium. The guide catheter can then be used as a conduit to introduce, remove, and exchange various therapeutic medical devices, such as guidewires, PTCA catheters, and stents, into and out of the branch vessels for treatment of disease states.

In most cases, the therapeutic devices that are introduced into the branch vessel navigate and cross through very tortuous, tight and narrowed passages, such as those that occur with a coronary stenosis. While attempting to push the therapeutic device forward across difficult lesions associated with coronary stenosis, there is a reactive force created on the therapeutic device that becomes applied to the guide catheter, resulting in pushing the guide catheter away from the branch artery. Frequently this reactive force, also referred to as "push back," overpowers the pre-formed distal curve shape as well as the stiffness of guide catheter, and causes the guide catheter to deflect and dislodge out of its seating in the ostium of the branch vessel. At this point, the therapeutic device can no longer be advanced forward as the guide catheter cannot provide the necessary support to the device. When this occurs, it necessitates re-seating of the guide catheter in the ostium or removal of all therapeutic devices, and the exchanging of the guide catheter to one with a more suitable curve shape.

A coaxial guide catheter extension has been developed to provide additional support to the guide wire. The extension extends beyond the parent guidewire down into the branch vessel, perhaps as much as 3 to 8 cm. This facilitates a method known as "deep seating," which relies on the additional extension length within the branch vessel to create resistance against the vessel walls, and thereby enhance support to the guide catheter. While this method provides some additional support, the reactive forces on the extension during therapeutic device manipulations may result in deflection of the extension and/or deflection and dislodging of the guide catheter, and thus, loss of support to the therapeutic devices.

In addition, many times the obstruction within the branch vessel is located very near the ostium of the vessel, for example, 10 mm away or less. In these situations, the use of the known extensions for deep seating is not possible given the short distance available within the vessel in which to seat the extension. Furthermore, in order to be effective, the coaxial guidewire extension must be stiffer than the therapeutic devices passing through the extension, and the introduction of the stiffer catheter extension relatively deeply down into a branch artery can result in damage to the vessel and surrounding tissue.

SUMMARY OF THE INVENTION

A coaxial stabilizing and sealing catheter provides increased support to a guide catheter that is seated in an ostium of a branch artery by extending through and out of a distal end of the guide catheter and anchoring in position within the branch vessel that is being treated. The stabilizing and sealing catheter includes, as part of a relatively flexible distal section, a balloon that is made of an elastomeric material. The balloon, which is inflated to contact the walls of the branch artery once the distal end section of the stabilizing and sealing catheter is in a desired position within the branch artery, locks the distal end of the stabilizing and sealing catheter in place to provide support to the therapeutic device(s) that are introduced into the branch artery through the distal end of the stabilizing and sealing catheter. Further, the balloon of the stabilizing and sealing catheter seals the artery to prevent blood from entering the artery.

In addition, the stabilizing and sealing catheter may include a sealing cuff at a proximal end of the distal section of stabilizing and sealing catheter. The sealing cuff provides a seal between the exterior of the stabilizing and sealing catheter and the interior of the guide catheter, such that any blood remaining and/or seeping into the sealed off artery can be aspirated out of the artery through the guide catheter.

Further, a fixation mechanism (e.g., a fixation balloon) may be included that is used to lock a guide wire within the guide catheter to assist in the exchanging of therapeutic devices being utilized.

BRIEF DESCRIPTION OF THE DRAWINGS

The invention description below refers to the accompanying drawings, of which:

FIG. 1 is an illustration depicting a stabilizing and sealing catheter constructed in accordance with the invention;

FIG. 2 is an illustration depicting a section of the stabilizing and sealing catheter of FIG. 1;

FIG. 4 is an illustration depicting an alternative arrangement of the stabilizing and sealing catheter;

FIG. 5 is an illustration depicting the stabilizing and sealing catheter of FIG. 4 more detail;

FIG. 6 is an illustration depicting an alternative arrangement of the stabilizing and sealing catheter;

FIG. 7 is an illustration depicting the stabilizing and sealing catheter of FIG. 6 more detail;

FIG. 9 is an illustration depicting a stabilizing and sealing catheter constructed in accordance with the invention;

FIG. 10 is an illustration depicting a section of the stabilizing and sealing catheter of FIG. 1;

DETAILED DESCRIPTION OF AN ILLUSTRATIVE EMBODIMENT

Figure 3:
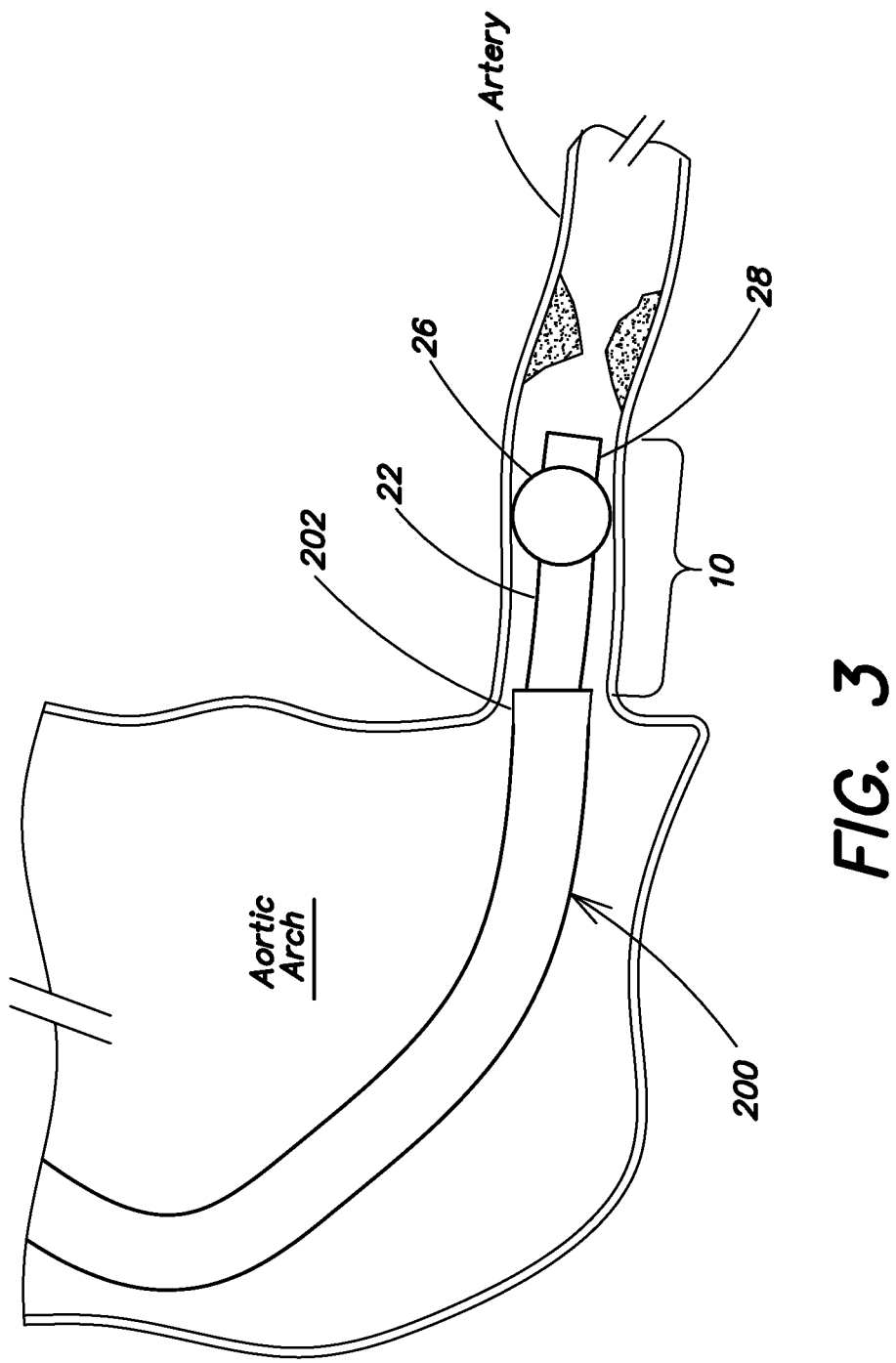
FIG. 3 is an illustration depicting the stabilizing and sealing catheter of FIG. 1 in place within a branch artery.

Referring to FIGS. 1-3, a coaxial stabilizing and sealing catheter 10 includes a relatively flexible distal end section 24 that supports a balloon 26. The stabilizing and sealing catheter 10 passes through a guide catheter 200 (FIG. 3) that is properly seated in an ostium, and the distal section 24 enters into and anchors in position within the branch artery vessel that is being treated. Once a distal tip 28 of the stabilizing and sealing catheter 10 is in a desired position within the branch artery, the balloon 26 is inflated to contact the wall of the branch artery. The inflated balloon 26 locks, and thus, stabilizes the distal section of the stabilizing and sealing catheter 10, which provides support to the therapeutic device(s) (not shown) that are introduced into and manipulated within the branch artery through the stabilizing and sealing catheter 10.

The distal section 24 of the stabilizing and sealing catheter 10 consists of a distal end of a dual lumen shaft 22. The shaft 22 supports the balloon 26 at a positioned near the distal tip 28 of the shaft. A main lumen 25 extends completely through the entire length of the stabilizing and sealing catheter 10 and includes a proximal end section 16 that extends outside of the body. The main lumen may include a low friction inner surface 15 that facilitates the movement of the therapeutic devices through the main lumen. A balloon inflation lumen 27 extends through the stabilizing and sealing catheter and terminates at the location of the balloon. The balloon inflation lumen 27, which includes a proximate section 14 that extends outside of the body, is used to both inflate and deflate the balloon 26.

The outer diameter of the dual lumen shaft of the stabilizing and sealing catheter 10 is sized so that the shaft can pass through the guide catheter 200. The inner diameter of the main lumen 25 is sufficiently large to accommodate the therapeutic devices that will be passed through the main lumen and into the branch vessel for treatment of the patient. The overall length of the stabilizing and sealing catheter 10 is slightly longer than the guide catheter 200, by 10 to 20 cm, such that the distal section 24 of the stabilizing and sealing catheter 10 can be directed out of the distal end 202 (FIG. 3) of the guide catheter 200 and positioned at a desired location within the branch vessel to be treated. The inner diameter of the balloon inflation lumen 27 is sufficiently small so as to avoid adversely affecting the passing of the therapeutic devices through the main lumen.

Once the tip 28 of the distal section 24 of stabilizing and sealing catheter 10 is in the desired location within the branch vessel, the balloon 26 is inflated via the balloon inflation lumen 27, to come into direct contact with the branch vessel wall. The inflated balloon 26 thereby anchors the distal section 24 of the stabilizing and sealing catheter 10 to provide a stabilized support for the introduction of the therapeutic devices into the branch vessel. As discussed below, the distal section of the stabilizing and sealing catheter 10 may, as needed, be seated only a relatively short distance into the branch vessel and yet still provide sufficient support to for the therapeutic devices.

The balloon 26 is made from a soft elastomeric material such as silicone, which can be inflated at very low pressures of 3 Atmospheres (ATM) or less, for example, 1 ATM, to prevent damage to the branch vessel wall while ensuring the anchoring strength is adequate to allow the anchored distal end to provide the necessary support to the therapeutic devices. A pressure relief valve (not shown) may be added within the balloon inflation lumen 27 to prevent over inflation of the balloon 26. Notably, the balloon 26 provides the anchoring strength whether fully or partially inflated.

The use of the elastomeric material for the balloon 26 allows the balloon to stretch up to a range of diameters during inflation and still provide sufficient anchoring strength. Accordingly, fixed sizes of balloons need not to be pre-determined for variable vessel diameters and patient anatomies. Thus, a single size balloon made of elastomeric material may be utilized with a variety of guide catheters utilized in a variety of patients.

The lengths of the balloon 26 and the tip 28 beyond the balloon are very short. The balloon may be 5 mm or less in length and the catheter tip may be 2 mm or less in length. The balloon may thus provide an anchor that sufficiently stabilizes the distal section of the stabilizing and sealing catheter 10 very near to ostial lesions that are, for example, 10 mm or less into the branch vessel from the ostium. The distal section of the stabilizing and sealing catheter 10 may instead be further or fully extended into the branch artery, and thus, anchored deeper into the branch artery as needed.

The anchoring of the distal section 24 of the stabilizing and sealing catheter 10 by the balloon 26, which is inflated within the branch artery, provides stability to the distal section that, in turn, provides support to the therapeutic devices that are passed through the stabilizing and sealing catheter to the branch artery. The distal section of the stabilizing and sealing catheter thus does not need to be particularly stiff. The stabilizing and sealing catheter dual lumen shaft may instead be made from a soft, flexible polymer that will easily traverse a tortuous vessel anatomy without causing damage to the vessel or surrounding tissue.

The tip 28 of the stabilizing and sealing catheter 10 may be made radiopaque through opacification agents, such as barium sulfate or bismuth subcarbonate added into the polymer or the addition of radiopaque marker bands, such as tungsten bands, affixed to the catheter shaft. As shown, marker bands 29 may be placed on the dual lumen shaft 22 at or near one or both ends of the balloon 26.

The stabilizing and sealing catheter 10 is utilized after the guide catheter 200 is introduced into an artery and seated within the ostium of the branch artery or vessel needing treatment. The stabilizing and sealing catheter, with the balloon 26 in a deflated state, is introduced through the seated guide catheter 200, and passed until the distal tip 28 of the stabilizing and sealing catheter 10 moves beyond a distal end 202 of the guide catheter 200 and into the branch vessel.

The stabilization and sealing catheter 10, which is 10 to 20 cm longer than the guide catheter 200, may be passed through the guide catheter until the tip 28 extends beyond the distal end 202 of the guide catheter 200 and into the branch vessel by the entire length of the distal section 24 or, as appropriate, the stabilization and sealing catheter may be passed through the guide catheter 200 until the distal tip is extend into the branch vessel a shorter distance to, for example, reach an obstruction in the branch artery. Once the tip 28 of the stabilizing and sealing catheter 10 is in the desired position within the branch artery, the balloon 26 is inflated through the balloon inflation lumen 27, until the balloon comes into direct contact with the wall of the branch vessel. As discussed, the anchoring balloon is inflated at a relatively low pressure, such as, for example, 1 ATM, to avoid damaging the walls of the branch vessel. The balloon 26 is inflated, fully or partially, to a diameter that corresponds to the particular constraints of the branch vessel in which the balloon is located. The balloon may be considered sufficiently inflated when, for example, resistance above a predetermined threshold is sensed at a syringe (not shown) that is used to inflate the balloon. Alternatively, or in addition, the pressure release valve (not shown) will ensure that only a desired pressure, in the example, 1 ATM, may be achieved in the balloon.

The therapeutic devices may then be introduced into the branch vessel through the main lumen 25 of the stabilization and sealing catheter 10. As discussed, the inflated balloon 26 anchors and stabilizes the distal section 24 of the stabilizing and sealing catheter, which, in turn, provides sufficient support to the therapeutic devices as the therapeutic devices are introduced to and manipulated and within the branch vessel.

The stabilizing and sealing catheter 10 has a proximal section 23 that is between 120 centimeters to 180 centimeters in length, and the distal section 24 which may be from 10 centimeters to 30 centimeters in length. The balloon 26 may be approximately 5 millimeters or less in length and may inflate to a maximum diameter of approximately 12 millimeters. The tip 28, which extends beyond the balloon 26, may be approximately 2 millimeters or less in length.

To remove the stabilizing and sealing catheter 10, the balloon 26 is deflated through the balloon inflation lumen 27, and the stabilizing and sealing catheter may be withdrawn from or along with the guide catheter 200 from the body.

As shown in the drawings, both the balloon inflation lumen 27 and the main lumen 25 are accessed from outside of the body and include luer fittings 13 that operate in a known manner. A bifurcation hub 20, which may, but need not, remain outside of the body, essentially combines the balloon inflation lumen 27 and the main lumen 25 into the one-piece co-axial dual lumen shaft 22. As discussed, the balloon inflation lumen 27 ends at the location of the balloon 26, to allow the balloon to be inflated and deflated, and the main lumen 25 extends through the balloon and to the tip 28 of distal section 24, to allow therapeutic devices to be provided through the entire length of the stabilizing and sealing catheter 10 and into the branch vessel.

Referring now to FIGS. 4 and 5, an alternative arrangement 30 of the stabilizing and sealing catheter includes an attachment 40 that consists of a dual lumen extrusion that provides a relatively short length of the dual lumen shaft 42. The attachment 40 attaches to a proximal section 46 of the balloon inflation lumen. The proximal section 46 is formed as a single lumen extrusion that is relatively long and has a diameter that is considerably smaller than the diameter of the attachment 40. The dual lumen extrusion includes a main lumen distal portion 45 and a balloon inflation lumen distal portion 47. The distal end of the proximal section 46 of the balloon inflation lumen extends into the distal portion 47, to provide a path that extends from outside the body to the location of the balloon 26 through which the balloon can be inflated by a syringe (not shown) that attaches outside of the body to the proximal section via the luer fitting 13. The distal portion 45 provides a passageway to the branch artery for the therapeutic devices.

In use, the arrangement 30 of the stabilizing and sealing catheter will again be introduced through the properly seated guide catheter 200. The small diameter proximal section 46 of the balloon inflation lumen will be used as a handle or rail, to advance and navigate the attachment 40 through the guide catheter 200 until the distal tip 48 extends beyond the distal end 202 of the guide catheter and into the branch artery of the patient to a desired position within the branch artery. Once the tip 48 of the stabilizing and sealing catheter is in the desired position, the balloon 26 that is located near the distal tip 48 of the attachment 40 is inflated via the balloon inflation lumen, to anchor the distal end of the attachment in place within the branch artery. The proximal end 46 of the dual lumen attachment 40 remains within the guide catheter, so that the stabilizing and sealing catheter acts essentially as an extension of the guide catheter 200.

After inflation of the balloon 26, the therapeutic devices (not shown) are passed through the guide catheter 200 and into and through the distal portion 45 the main lumen in the attachment 40 and ultimately into the patient's vasculature for treatment.

The length of the distal dual lumen extrusion that forms the attachment 40 is approximately 25 cm while the length of the proximal section 46 of the balloon inflation lumen, that is, the single lumen extrusion, is approximately 130 cm to allow the proximal end of the lumen that supports the luer fitting 13 to extend beyond the proximal end of the guide catheter 200. The user can then inflate and deflate the balloon via a syringe (not shown) attached via the luer fitting.

The diameter of the attachment 40 is sized to fit closely, but without interference, within the guide catheter 200. For example, the attachment 40 is sized for use with an 8 French guide catheter, which has an inner diameter on the order of 0.090", and has an outer diameter on the order of 0.080". The outer diameter of the attachment 40 is sized to maximize the inner diameter of the distal portion 45 of main lumen while permitting smooth movement of the attachment through the inside of the guide catheter. In the example above, the inner diameter of the distal portion 45 of the main lumen can be 0.050" or greater.

The outer diameter of the proximal section 46 of the balloon inflation lumen, that is, the single lumen extrusion, is considerably smaller than the outer diameter of the dual lumen attachment 40. The proximal section may, for example, have a diameter of 0.025" or less, to provide ample space for the therapeutic devices to be passed alongside the proximal section 46 through the guide catheter 200.

A proximal leading edge 44 of the distal portion 45 of the main lumen of the attachment 40 is tapered inwardly, such that the therapeutic devices can easily enter into the distal portion 45 of the main lumen as they are advanced through the guide catheter 200.

The dual lumen attachment 40 may be relatively flexible, while the proximal single lumen section 46 is stiffer, to direct and advance the distal portion of the stabilizing and sealing catheter through and out of the guide catheter. Stiffening of the proximal portion can be accomplished through use of a higher durometer polymer or the addition of a wire braid within the wall of the extrusion. Alternatively, a small diameter stiffening wire may be added within the single lumen or the extrusion wall and/or a metal tube made from stainless steel or nitinol may be used as the proximal single lumen portion.

Radiopaque marker bands 49 are arranged near the balloon 26 and one or more additional radiopaque marker bands (not shown) may also be added near the proximal end of the attachment 40, that is, the dual lumen extrusion, to act as an identifier to the physician so that he/she is aware of the location of the distal section of the stabilizing and sealing catheter. As shown in FIG. 5, an inlet/outlet 43 in the distal portion 47 balloon inflation lumen provides access to the balloon 26.

Figure 8:
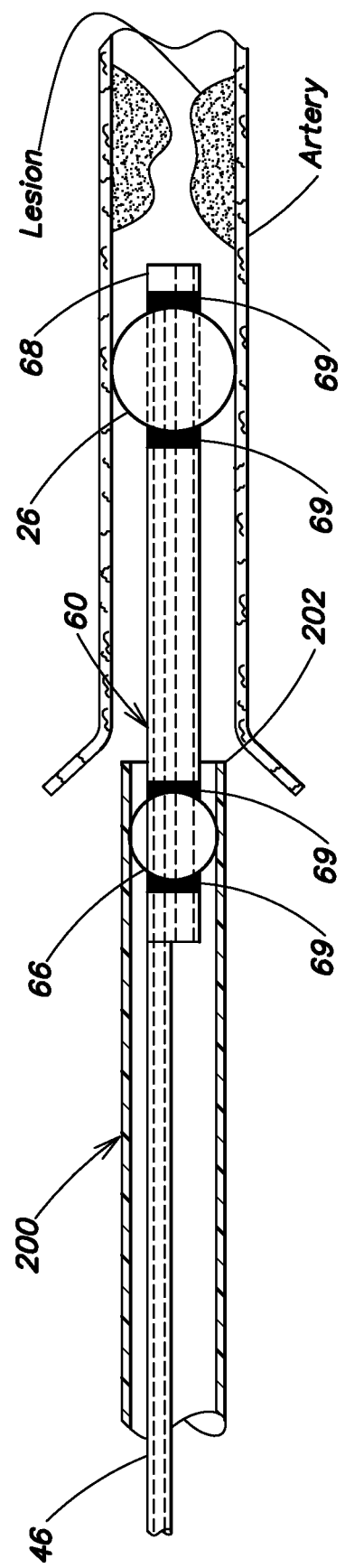
FIG. 8 is an illustration depicting the stabilizing and sealing catheter of FIG. 6 in place within a branch artery.
Figure 11:
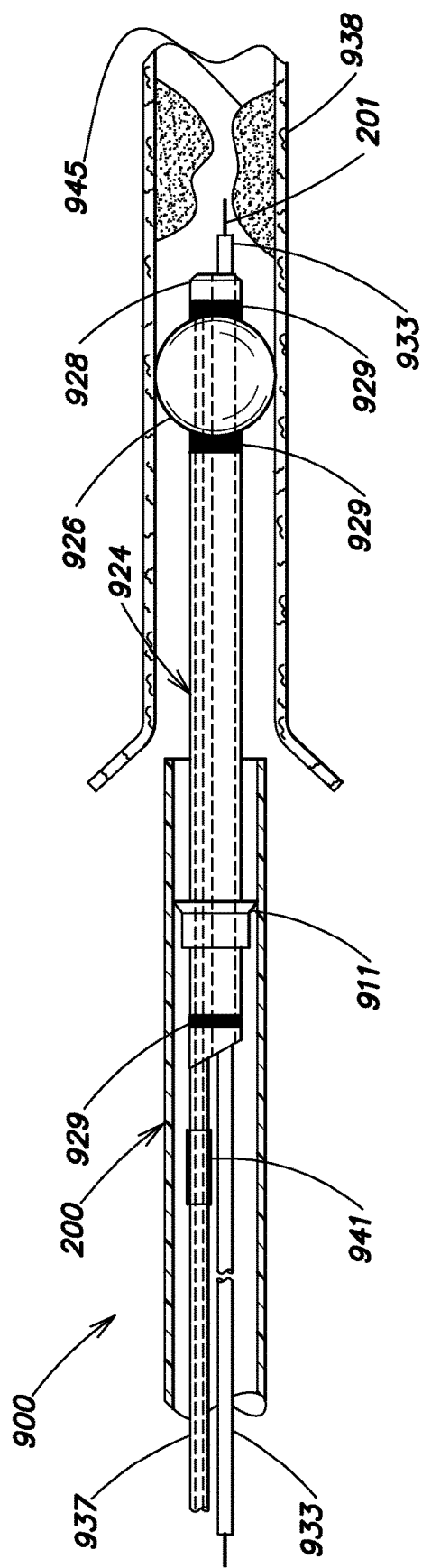
FIG. 11 is an illustration depicting the stabilizing and sealing catheter of FIG. 1 in place within a branch artery.
Figure 12:
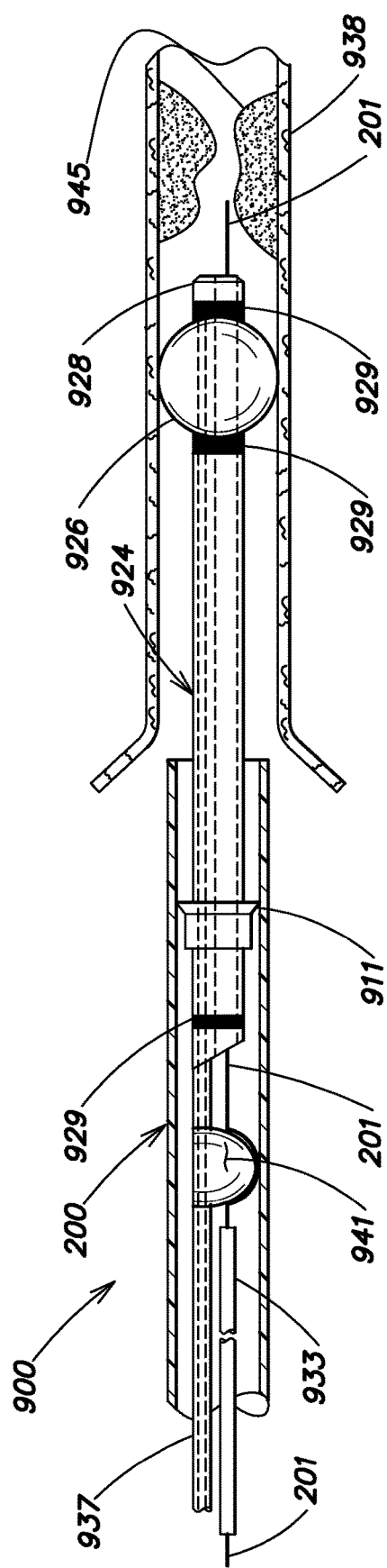
FIG. 12 is an illustration depicting the stabilizing and sealing catheter of FIG. 1 in place within a branch artery.
Figure 13:
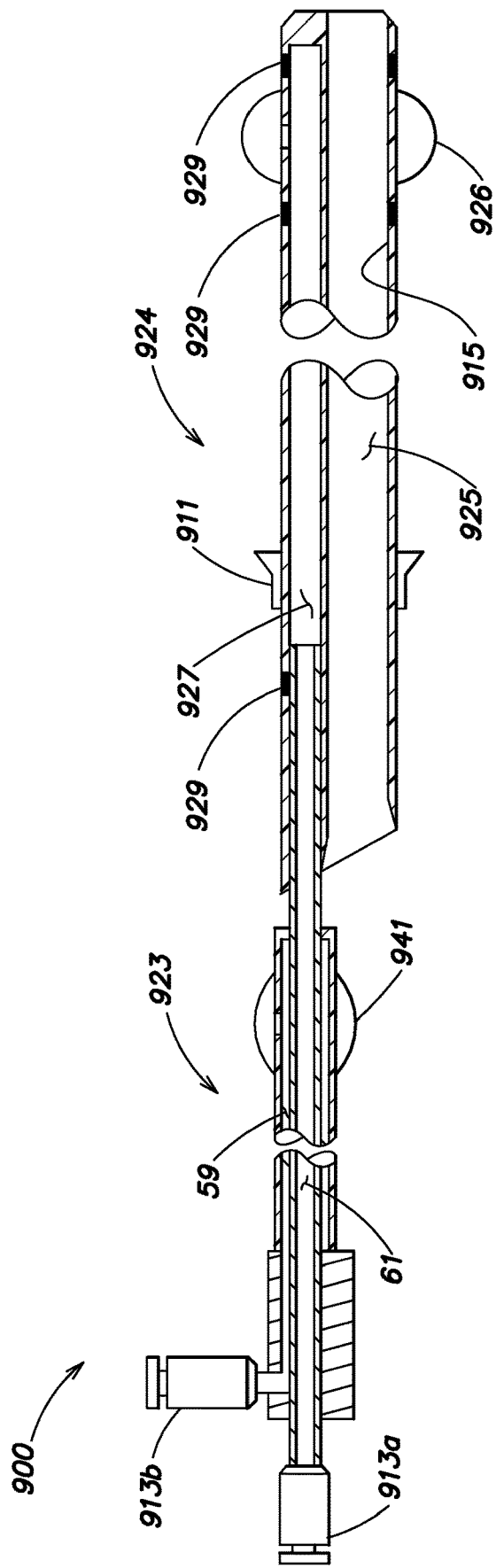
FIG. 13 is an illustration depicting a stabilizing and sealing catheter constructed in accordance with the invention.

Referring now to FIG. 6-8, another alternative arrangement 50 of the stabilizing and sealing catheter includes a balloon 26 near a distal tip 68 and an additional anchoring balloon 66 at a proximal end 64 of a dual lumen attachment 60 that provides a dual lumen shaft 62. The additional balloon 66 is inflated within the guide catheter 200 to come into contact with the guide catheter, and anchor the attachment 60 to the guide catheter. In this way, the stabilizing and sealing catheter becomes integral with the guide catheter and acts essentially as a relatively flexible extension of the guide catheter into the branch artery. With the distal anchoring balloon 26 also inflated within the branch vessel, maximum stabilization is achieved over the entire system of stabilizing and sealing catheter and guide catheter.

The additional balloon 66 may, but need not, be a fixed size balloon. The balloon may be relatively short in length, for example, 3 to 5 mm, and have a maximum inflated diameter not to exceed 0.090" (about 2.5 mm), which is the inner diameter of an 8F guide catheter. However, the balloon 66 may have a smaller maximum inflatable size that corresponds to the relatively small space between the stabilizing and sealing catheter and the guide catheter. The balloon 66 may, but need not, be made of elastomeric material.

As shown in FIG. 7, the attachment 60 includes distal portions 65 and 67 of a main thru lumen and a balloon inflation lumen. A proximal end 64 of the distal portion 65 is tapered to allow easy access for the therapeutic devices that are passed through the guide catheter 200 and then the distal portion 65 to the branch artery.

The distal portion 67 of the balloon inflation lumen includes inlet/outlets 63 for the inflation and deflation of the balloons 26 and 66. Since both balloons 26 and 66 are connected to the distal portion 67 of the balloon inflation lumen, the two balloons will inflate together. Radiopaque markers 69 may be provided near each of the balloons.

Referring to FIGS. 9-13, a coaxial stabilizing and sealing catheter 900 includes a proximal section 923 that includes a proximal sealing catheter shaft 937 and a relatively flexible distal end section 924 that supports a balloon 926. The stabilizing and sealing catheter 900 passes through a guide catheter 200 having a guide wire 201 (FIGS. 11 and 12) that is properly seated in an ostium, and the distal section 924 enters into and anchors in position within the branch artery vessel 938 that is being treated, for example, remove a blockage 945 from the artery. Once a distal tip 928 of the stabilizing and sealing catheter 900 is in a desired position within the branch artery 938, the balloon 926 is inflated to contact the wall of the branch artery 938. The inflated balloon 926 locks, and thus, stabilizes the distal section 924 of the stabilizing and sealing catheter 900, which provides support to a therapeutic device 933 (FIGS. 11-12) that is introduced into and manipulated within the branch artery 938 through the stabilizing and sealing catheter 900. In addition, the inflated balloon 926 of the stabilizing and sealing catheter 900 seals the artery 938 to prevent blood from entering the artery 938.

A sealing cuff 911 at a proximal end of the distal section 924 provides a seal between the exterior of the stabilizing and sealing catheter 900 and the interior of the guide catheter 200, such that any blood remaining and/or seeping into the sealed off artery 938 can be aspirated out of the artery 938 through the guide catheter 200. Specifically, a syringe or other suction device (not shown) may be connected to the proximal end of the guide catheter 200 and aspiration may be generated to remove blood and/or a thrombus from the artery 938 during treatment. The aspiration device may be locked or held under vacuum so that a continuous suction is being applied to the artery 938.

In an embodiment, the sealing cuff 911 is a polymer band with slightly flared distal edge. The distal edge is radially deflectable inwardly onto the stabilizing and sealing catheter 900 during insertion and remains outwardly protruding within the guide catheter 200 so that the distal edge is in contact with the inner wall of the guide catheter 200. In an embodiment, the flared distal edge is of relatively short length so that it does not impede movement of the stabilizing and sealing catheter 900 within the guide catheter 200. The flared edge is oriented distally so that when aspiration is applied to the guide catheter 200 at the proximal end, the flared edge will continue to expand outwardly, to maintain the seal with the guide catheter 200.

The distal section 924 of the stabilizing and sealing catheter 900 comprises a dual lumen shaft 922. The dual lumen shaft 922 supports the balloon 926 at a position near the distal tip 928 of the shaft. A main lumen 925 extends completely through the entire length of the stabilizing and sealing catheter 900. The main lumen 925 may include a low friction inner surface 915 that facilitates the movement of the therapeutic devices through the main lumen 925.

A balloon inflation lumen 927 extends through the stabilizing and sealing catheter and terminates at the location of the balloon 926. The balloon inflation lumen 927 is sized to fit a proximal sealing catheter shaft 937 that extends outside of the body and is used to both inflate and deflate the balloon 926 and the fixation balloon 941. In an embodiment, the proximal sealing catheter shaft 937 is a dual lumen shaft. A first lumen 61 (FIG. 13) is connected to the balloon 926, through lumen 927 of the stabilizing and sealing catheter 900, and inflates and deflates the balloon 926. A second lumen 59 (FIG. 13) is connected to the fixation balloon 941 at the distal end of the proximal section 923 and inflates and deflates the fixation balloon 941. The respective balloons are inflated and deflated through use of the respective luer fittings 913a and 913b coupled to the proximal sealing catheter shaft 937.

The second lumen 59 for the fixation balloon 941 may be made from a polymer material that allows for the inflation of the fixation balloon at high pressures to ensure the guide wire is locked in place. The first lumen 61 for the balloon 926 may be made from a metal tube of stainless steel or nitinol material that will provide rigidity for directing and delivering the stabilizing and sealing catheter 900. The proximal sealing catheter shaft 937 may be used as a handle or rail, to advance and navigate the stabilizing and sealing catheter 900 through the guide catheter 200 and out into the artery 938 (vessel) of the patient.

Figure 14:
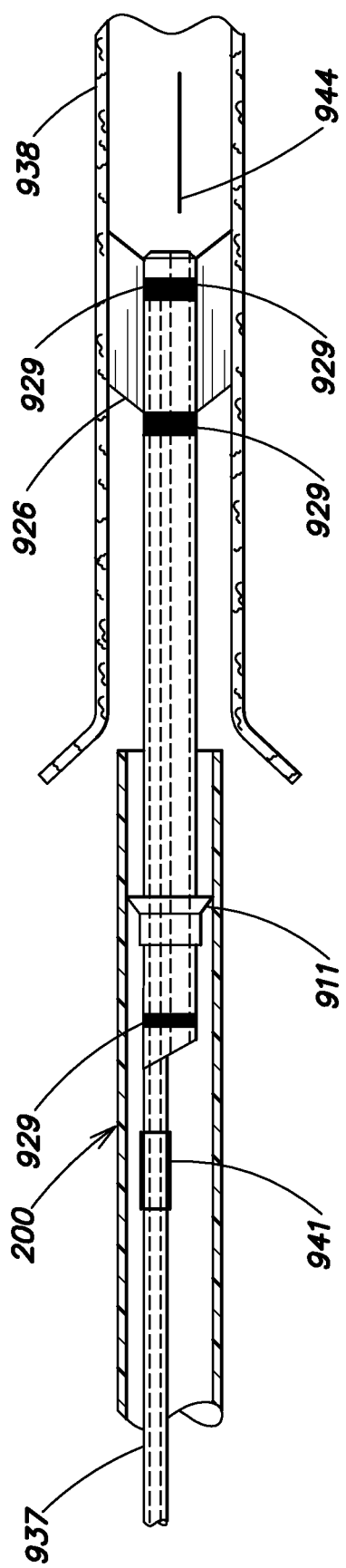
FIG. 14 is an illustration depicting a stabilizing and sealing catheter constructed in accordance with the invention.

Once the tip 928 of the distal section 924 of stabilizing and sealing catheter 900 is in the desired location within the branch vessel 938, the balloon 926 is inflated, via the balloon inflation lumen 927, to come into direct contact with the branch vessel wall. The inflated balloon 926 thereby anchors the distal section 924 of the stabilizing and sealing catheter 900 to provide a stabilized support for the introduction of the therapeutic device 933 into the branch vessel via the main lumen 925. The distal section 924 of the stabilizing and sealing catheter 900 may, as needed, be seated only a relatively short distance into the branch vessel 938 and yet still provide sufficient support to for the therapeutic device 933. In addition, the inflated balloon 926 seals the artery 938 to prevent blood from entering the artery 938. In an embodiment, and as illustrated in FIG. 14, the balloon 926 may be shaped such that it forms a reverse funnel when inflated, which may direct a retrograde wire 944 into the stabilizing and sealing catheter 900.

In addition, one or more radiopaque markers bands 929, such as tungsten bands or platinum bands, are affixed to the stabilizing and sealing catheter 900. The radiopaque marker bands 929 may be used to identify the location of the distal tip, the sealing balloon, and the proximal end of the distal catheter segment. In addition, exit markers 931 may be included on the proximal section 923.

Further, and once in the desired location, the sealing cuff 911 provides a seal between the exterior of the stabilizing and sealing catheter 900 and the interior of the guide catheter 200, such that any blood remaining and/or seeping into the sealed off artery 938 can be aspirated out of the artery 938 through the guide catheter 200.

When exchanging of devices is necessary, the therapeutic device 933 to be removed is withdrawn over the guide wire 201 and back into the guide catheter 200 until the distal end of the therapeutic device 933 is proximally beyond the fixation balloon 941. The fixation balloon 941 is then inflated, at a high pressure, for example, utilizing the proximal sealing catheter shaft 937 to lock the guide wire 201 against the wall of the guide catheter 200, thereby preventing axial movement of the guide wire 201, as seen in FIG. 14, such that the therapeutic device 933 can be securely removed. A secondary therapeutic device (not shown) may then be passed onto the locked guide wire 201 and directed down towards the fixation balloon 941 until the proximal end of the guide wire 201 becomes accessible outside of the proximal end of the secondary therapeutic device. The fixation balloon 941 can then be deflated utilizing the proximal sealing catheter shaft 937 thereby allowing the secondary therapeutic device to be further directed into the branch vessel 938 to provide a treatment.

To remove the stabilizing and sealing catheter 900, the balloon 926 and fixation balloon 941 are deflated, and the stabilizing and sealing catheter may be withdrawn from or along with the guide catheter 200 from the body.

The foregoing description described certain exemplary embodiments. It will be apparent, however, that other variations and modifications may be made to the described embodiments, with the attainment of some or all of their advantages. Accordingly, the foregoing description is to be taken only by way of example, and not to otherwise limit the scope of the disclosure.

What is claimed is:

1. A stabilizing and sealing catheter for use with a guide catheter including:
   a proximal section, and
   a distal section that includes a dual lumen shaft that is divided into a main lumen and a balloon inflation lumen that are separate and distinct, the dual lumen shaft supporting at least a balloon near a distal tip of the dual lumen shaft, wherein a length and an inner diameter of the main lumen are greater than the length and the inner diameter of the balloon inflation lumen, wherein the main lumen, at a proximate end of the distal section, is tapered inwardly along an entire inner circumference of a portion of an interior of the main lumen, and wherein the main lumen is open and passes through the balloon and the balloon inflation lumen passes through the balloon and terminates,
   the proximal section and distal section having outer diameters that are sized to pass through an inner diameter of the guide catheter, and have lengths that together are sufficiently long that at least the balloon and the distal tip of the distal section extend beyond a distal end of the guide catheter when the stabilizing and sealing catheter passes through the guide catheter,
   wherein the distal section supports at the proximate end a second balloon, the second balloon being located along the distal section to remain within the guide catheter when the balloon and the distal tip of the distal section extend beyond the distal end of the guide catheter, wherein a radiopaque marker is included on the dual lumen shaft on either side of the balloon near the distal tip and the second balloon, and
   wherein the balloon and the second balloon are inflated and deflated together through use of the balloon inflation lumen.

2. The stabilizing and sealing catheter of claim 1 wherein the proximal section includes a single balloon inflation lumen and the distal section is a dual lumen attachment that includes the main lumen that is sized to allow therapeutic devices to pass through and the balloon inflation lumen that is narrower than the main lumen and attaches to the proximal section that is the single balloon inflation lumen.

3. The stabilizing and sealing catheter of claim 1 wherein the main lumen includes a low friction inner surface that facilitates movement of therapeutic devices to pass through the main lumen.

4. The stabilizing and sealing catheter of claim 1 wherein the balloon is made from an elastomeric material.

5. The stabilizing and sealing catheter of claim 1 wherein the distal tip is radiopaque.

6. The stabilizing and sealing catheter of claim 1 wherein the balloon inflation lumen ends at a location of the balloon and the main lumen extends through the balloon and to the distal tip.

7. A stabilizing and sealing catheter for use with a guide catheter including:
   a proximal section including a proximal sealing catheter shaft and a fixation balloon, and
   a distal section that includes a main lumen that houses a guide wire and a balloon inflation lumen as part of a dual lumen shaft that supports at least one balloon near a distal tip of the shaft and further including a sealing cuff at a proximal end of the distal section between the fixation balloon and the balloon near the distal tip of the shaft, wherein the fixation balloon is configured to be inflated and lock the guide wire, which extends through the main lumen and the guide catheter, against an inner wall of the guide catheter, the proximal section and distal section having outer diameters that are sized to pass through an inner diameter of the guide catheter, and have lengths that together are sufficiently long that at least the balloon and the distal tip of the distal section extend beyond a distal end of the guide catheter when the stabilizing and sealing catheter passes through the guide catheter, and wherein the sealing cuff includes a flared distal edge that remains outwardly protruding and a flared circumference of the flared distal edge makes contact with an inner circumference of the inner wall of the guide catheter to form a seal.

8. The stabilizing and sealing catheter of claim 7 wherein the balloon is inflated and deflated utilizing the proximal sealing catheter shaft and the fixation balloon is inflated and deflated utilizing the proximal sealing catheter shaft.

9. The stabilizing and sealing catheter of claim 8 wherein the proximal sealing catheter shaft is passed within the balloon inflation lumen to inflate and deflate the balloon and the fixation balloon.

10. The stabilizing and sealing catheter of claim 7 wherein the flared distal edge remains outwardly protruding and makes contact with the inner wall of the guide catheter to form a seal during insertion of the stabilizing and sealing catheter into the guide catheter.

11. The stabilizing and sealing catheter of claim 7 wherein the balloon when inflated forms a reverse funnel that directs a retrograde wire into the stabilizing and sealing catheter.

12. The stabilizing and sealing catheter of claim 7 wherein the main lumen includes a low friction inner surface that facilitates movement of therapeutic devices to pass through the main lumen.

13. The stabilizing and sealing catheter of claim 7 wherein the balloon is made from an elastomeric material.

14. The stabilizing and sealing catheter of claim 7 wherein the distal tip is radiopaque.

15. The stabilizing and sealing catheter of claim 7 wherein the balloon inflation lumen ends at a location of the balloon and the main lumen extends through the balloon and to the distal tip.

16. The stabilizing and sealing catheter of claim 7 wherein the proximal sealing catheter shaft is a different dual lumen, wherein a first lumen of the different dual lumen is utilized to inflate and deflate the balloon and a second lumen of the different dual lumen is utilized to inflate and deflate the fixation balloon.

17. The stabilizing and sealing catheter of claim 16 wherein the second lumen, of the different dual lumen utilized to inflate and deflate the fixation balloon, is made of a polymer.

* * * * *